United States Patent [19]
Heggie et al.

[11] Patent Number: 4,968,654
[45] Date of Patent: * Nov. 6, 1990

[54] PREPARATION OF A NEW CATALYST CONTAINING RHODIUM

[75] Inventors: William Heggie, Barreiro; Philip R. Page, Sintra; Ivan Villax, Codex, all of Portugal

[73] Assignee: Plurichemie Anstalt, Portugal

[*] Notice: The portion of the term of this patent subsequent to Oct. 29, 2002 has been disclaimed.

[21] Appl. No.: 325,445

[22] Filed: Mar. 20, 1989

Related U.S. Application Data

[62] Division of Ser. No. 50,931, May 15, 1987, Pat. No. 4,863,639.

[30] Foreign Application Priority Data

Mar. 25, 1987 [PT] Portugal .................................. 74303

[51] Int. Cl.$^5$ ...................... B01J 31/24; C07C 103/19
[52] U.S. Cl. ........................................ 502/166; 556/23
[58] Field of Search .......................... 502/166; 556/23

[56] References Cited

U.S. PATENT DOCUMENTS 4,550,096 10/1985 Page et al. ........................... 502/166
4,743,699 5/1988 Page et al. ....................... 502/166 X

*Primary Examiner*—Patrick P. Garvin
*Attorney, Agent, or Firm*—Ostrolenk, Faber, Gerb & Soffen

[57] ABSTRACT

The present invention refers to the compounds ($\mu$-hydrazine-N$^1$:N$^2$)-bis[bis(triphenylphosphine)-chlororhodium (I)] and di($\mu$-hydrazine-N$^1$:N$^2$)-bis[bis(triphenylphosphine)rhodium (I)] dichloride, which are homogenous hydrogenation catalysts and their application in the hydrogenation of the exocyclic methylene group of acid addition salts of 6-demethyl-6-deoxy-6-methylene-5-hydroxytetracycline (methacycline) to prepare $\alpha$-6-deoxy-5-hydroxytetracycline (doxycycline).

7 Claims, No Drawings

PREPARATION OF A NEW CATALYST CONTAINING RHODIUM

This is a division of application Ser. No. 07/050,931 filed May 15, 1987 and now U.S. Pat. No. 4,863,639.

The present invention relates to the compound di(μ-hydrazine-N¹:N²)-bis[bis(triphenylphosphine)rhodium (I)]dichloride, which is an homogeneous hydrogenation catalyst and its application in the hydrogenation of the exocyclic methylene group of acid addition salts of 6-demethyl-6-deoxy-6-methylene-5-hydroxytetracycline (methacycline) to prepare α-6-deoxy-5-hydroxytetracycline (doxycycline).

Doxycycline is a wide-spectrum antibacterial agent, with widespread application in the treatment of numerous infections in humans and in animals. The hydrogenation of the exocyclic methylene group of methacycline can produce two epimers. The α-6-epimer is doxycycline, whilst the β-6-epimer, called 6-epi-doxycycline, is devoid of clinical utility. Thus, it is important that the hydrogenation does not co-produce this β-6-epimer. In fact, the British Pharmacopoeia 1980 established a limit for the content of 6-epi-doxycycline in doxycycline of 2%.

In the prior art, doxycycline was first described in 1960 in U.S. Pat. No. 3,200,149. Since that time many methods have been described for its preparation, in all of which the modification of the catalytic system has been described as producing improved yields or a purer product. In the field of heterogeneous catalysis, U.S. Pat. Nos. 3,444,198, 3,849,491, 3,954,862 and 4,597,904 and the report in Chemical Abstracts 86, 89476 f (1977) of Hungarian Patent No. 12,042 have all taught improved methods for the preparation of doxycycline and its analogues.

The first use of homogeneous catalysis was described in U.S. Pat. No. 4,207,258 (Italian priority 1972), wherein the catalyst was a complex of rhodium with tertiary phosphine, arsine and stibine ligands. U.S. Pat. No. 3,962,331 extended the above process to the simultaneous reductive dehalogenation and hydrogenation of an 11a-halomethacycline. French Patent No. 2,216,268 later disclosed the use of the same catalyst.

Since that time, other patents have appeared such as U.S. Pat. Nos. 3,907,890, 4,001,321 and 3,962,131 all describing variations in the catalytic system and claiming improved yields and stereospecificity.

The first homogeneous hydrogenation catalysts of the type of tertiary phosphine-hydrazino-rhodium complexes were described in U.S. Pat. No. 4,550,096. These were prepared either by reacting a rhodium salt, specifically rhodium trichloride, with a tertiary phosphine and a hydrazine, or by reacting a rhodium complex, such as tris(triphenylphosphine)chlororhodium, with a hydrazine. These complexes allowed the preparation of doxycycline, containing less than 1% of the undesired 6-epi-doxycycline, in high yield using considerably less rhodium than had been taught in the prior art.

These complexes have proved to be very satisfactory catalysts for the hydrogenation of methacycline especially if an excess of a tertiary phosphine is included in the hydrogenation mixture as a promoter.

The exact chemical formulae and structures of the catalysts of this U.S. Patent were not disclosed in the patent, but reported elemental analyses showed some significant variability in elemental composition indicating variations in constitution.

It has now been found that, by changing the process conditions used in the U.S. Patent, a very satisfactory new catalyst can be made which has a well defined structure. It is advantageous, from general considerations, to be able to use catalysts of precisely known formula and structure, and furthermore the new catalyst is very effective for the hydrogenation of methacycline without the need to add any excess tertiary phosphine.

According to the present invention, there is provided a process for the preparation of a complex of rhodium and hydrazine, containing triphenylphosphine and chlorine, useful as a homogeneous hydrogenation catalyst, which comprises reacting tris(triphenylphosphine)chlororhodium with hydrazine or hydrazine hydrate in methanol under an inert atmosphere, stirring the reaction mixture at room temperature, or refluxing it and then recovering the solid complex from the mixture, characterised in that the reaction is conducted in the absence of oxygen using degassed methanol, and wherein a complex of formula I:

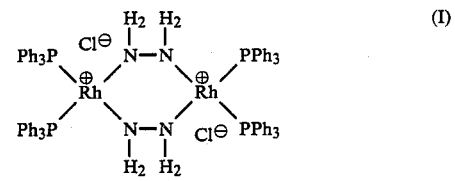

wherein Ph is phenyl, is obtained when for each mole of tris(triphenylphosphine)chlororhodium at least one mole of hydrazine is used, and the reaction mixture is stirred at room temperature for a prolonged period or refluxed, followed by standing at room temperature for at least 12 hours in order to form crystals of the complex.

The invention includes the new catalyst compound of formula I per se, and also a process for the catalytic stereospecific hydrogenation of an acid addition salt of 6-demethyl-6-deoxy-6-methylene-5-hydroxytetracycline to prepare α-6-deoxy-5-hydroxytetracycline, wherein the hydrogenation is carried out at a temperature between 60° C. and 100° C., at a pressure of 1 to 10 kg/cm² until the reaction is complete, followed by isolation of the thus formed compound by known processes, characterised by using the catalyst prepared by the process of the invention.

In the process of the invention for making the new catalyst, the tris(triphenylphosphine)chlororhodium must be freshly prepared, and stored and manipulated under an inert atmosphere. The preparation and isolation of the complex compound must be carried out under an inert atmosphere with complete exclusion of air and in degassed reaction media, followed by drying under an inert atmosphere or in vacuum. After eventual purification, the complex obtained is of a uniform composition and well defined formula.

According to the present invention, a catalyst of the formula I is obtained by reacting, under an inert atmosphere at room temperature for a prolonged period or at reflux, one mole of tris(triphenylphosphine)chlororhodium with at least one mole of hydrazine in degassed methanol, followed by standing at room temperature for at least 12 hours, for example one to two days.

The formula has been unequivocally established by X-ray crystallography.

It is to be noted that this structure falls within the general structure given in U.S. Pat. No. 4,550,096.

The catalyst of the invention is fully active in the hydrogenation of methacycline to doxycycline. Furthermore, it is not necessary to add excess triphenylphosphine to ensure a near stoichiometric yield of the required α-epimer.

The conditions of preparation of the catalyst of the present invention are illustrated in Example 1. The tris(triphenylphosphine)chlororhodium and hydrazine can be reacted in the molecular proportion corresponding to their respective formulae, but it is advantageous to use hydrazine in excess so as to obtain the maximum yield in relation to the expensive rhodium complex.

The hydrazine can be used as either the anhydrous base or as the monohydrate. It has been verified that the anhydrous base allows shorter reaction times.

Tris(triphenylphosphine)chlororhodium (1 mole) and hydrazine hydrate (3 moles) are refluxed in degassed methanol under a nitrogen atmosphere, in adequate equipment, followed by standing at room temperature, filtration and drying under vacuum, to give yellow crystals of the compound. In contrast, cooling, preferably after concentration, favours the isolation of a different yellow solid and should be avoided.

The complex of formula I is stable for at least one month, providing it is stored under nitrogen at reduced temperatures. After this period, slightly diminished catalytic activity is sometimes observed. Therefore, the complex should be in preference freshly prepared to obtain the best hydrogenation results. Alternatively, it can be prepared immediately prior to use and then employed without isolation by addition to the hydrogenation reaction mixture, whereby equally good results can be achieved.

As already indicated, the hydrazino-rhodium complex of the present invention is an efficient homogeneous stereospecific hydrogenation catalyst, in general. Its use is fully described in U.S. Pat. No. 4,863,639.

The following example serves to illustrate the present invention, without in any way limiting the scope thereof.

EXAMPLES (1) Preparation of di(μ-hydrazine-$N^1$:$N^2$)-bis[bis(triphenylphosphine)-rhodium (I)]dichloride Tris(triphenylphosphine)chlororhodium (1.05 g; 1.13 mmoles) was placed in a two necked round bottom flask. The solid was stirred under vacuum for 30 minutes and then under an atmosphere of nitrogen. Dry, degassed methanol (170 ml) was added and the mixture was stirred for 15 minutes. A methanolic solution of hydrazine hydrate (30 ml of a methanolic solution containing 5.91 mg/ml; 3.54 mmoles) was added. The reaction mixture was refluxed for 2 hours. Upon standing overnight, yellow crystals were deposited, which were filtered and dried under vacuum.

A single crystal of approximate dimensions 0.3 mm×0.15 mm×0.1 mm was sealed under argon in a thin walled glass capillary. Unit cell and intensity data were obtained using an Enraf-Nonius CAD4 diffractometer, following standard procedures. Details of the experimental features are as follows:

Crystal data: $[C_{72}H_{68}N_4P_4Rh_2].[Cl]_2 \cdot CH_3OH$, Mw=1422.02, monoclinic, space group P2$_1$/n, a=15.009(3)Å, b=13.294(2)Å, c=18.391(4)Å, β=108.9(1)°, V=3471.9Å$^3$, Z=2, Dc=1.36 g.cm$^{-3}$, μ(Mo—Kα)=6.14 cm$^{-1}$.

Data collection: Data were recovered for 1.5°≦θ≦21° at room temperature, 291° K. and corrected for absorption empirically. 3716 intensities were measured, of which 1805 were considered observed [I>1.5σ(I)] and used in the analysis.

The structure was solved via the heavy atom method and refined by full matrix least squares. In view of the small number of observed data, the structure was refined in the anisotropic approximation, but with the phenyl groups defined as rigid bodies. No hydrogens were confidently located on the hydrazine nitrogen atoms and none were included. The final R value is 0.06.

The complex was found to contain a dimeric cation in which two $(Ph_3P)_2Rh$ units were linked together by two bridging hydrazine molecules, as shown in Ia:

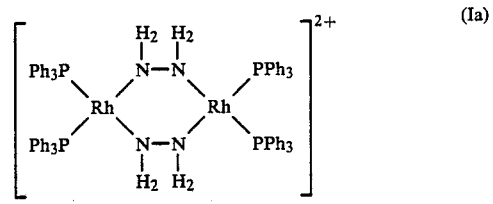

The rhodium centres have the expected square planar configuration, with the Rh—P and Rh—N distances being normal. The central $Rh_2N_4$ ring has a chair conformation, compatible with its centrosymmetric nature.

We claim:

1. A process for the preparation of a complex of rhodium and hydrazine, containing triphenylphosphine and chlorine, useful as a homogeneous hydrogenation catalyst, which comprises reacting tris(triphenylphosphine)chlororhodium with hydrazine or hydrazine hydrate in methanol under an inert atmosphere, stirring the reaction mixture at room temperature, or refluxing it, and then recovering the solid complex from the mixture, characterised in that the reaction is conducted in the absence of oxygen using degassed methanol, and wherein a complex of formula (I):

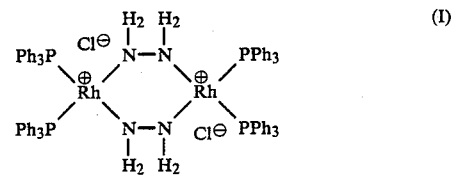

wherein Ph is phenyl, is obtained when for each mole of tris(triphenylphosphine)chlororhodium at least one mole of hydrazine is used, and the reaction mixture is stirred at room temperature for a prolonged period or refluxed, followed by standing at room temperature for at least 12 hours in order to form crystals of the complex.

2. A process according to claim 1, characterised by the fact that the inert atmosphere is nitrogen.

3. A process according to claim 1, characterised by the fact that the hydrazine is the anhydrous base or the monohydrate.

4. A process according to claim 2, characterized by the fact that the hydrazine is the anhydrous base or the monohydrate.

5. A process according to claim 1, wherein the catalyst is prepared from ½ to 4 moles of hydrazine per mole of tris(triphenylphosphine)chlororhodium.

6. A process according to claim 5, wherein 3 moles of hydrazine are used per mole of tris(triphenylphosphine)chlororhodium.

7. The compound di(μ-hydrazine-$N^1$:$N^2$)-bis[bis(triphenylphosphine)-rhodium (I)]dichloride.

* * * * *

UNITED STATES PATENT AND TRADEMARK OFFICE
CERTIFICATE OF CORRECTION

PATENT NO. : 4,968,654

DATED : November 6, 1990

INVENTOR(S) : William Heggie et al.

It is certified that error appears in the above-identified patent and that said Letters Patent is hereby corrected as shown below:

On Title page: [75]"inventors:", after "Portugal" read --; Michael Hursthouse, Chelmsford; Richard Somerville, Hornchurch, both of England.--

In the headings under "Assignee" for "Portugal" read --Liechtenstein--.

Signed and Sealed this

Twelfth Day of May, 1992

Attest:

DOUGLAS B. COMER

*Attesting Officer*      *Acting Commissioner of Patents and Trademarks*